US00PP29851P2

(12) United States Plant Patent
Schroll

(10) Patent No.: US PP29,851 P2
(45) Date of Patent: Nov. 20, 2018

(54) ***HYDRANGEA* PLANT NAMED 'SCHROLL85-09-02'**

(50) Latin Name: *Hydrangea macrophylla*
Varietal Denomination: SCHROLL85-09-02

(71) Applicant: Soren Schroll, Odense SV (DK)

(72) Inventor: Soren Schroll, Odense SV (DK)

(73) Assignee: Schroll Management ApS, Odense SV (DK)

( * ) Notice: Subject to any disclaimer, the term of this patent is extended or adjusted under 35 U.S.C. 154(b) by 0 days.

(21) Appl. No.: 15/732,793

(22) Filed: Dec. 28, 2017

(51) Int. Cl.
*A01H 5/02* (2018.01)
*A01H 5/00* (2018.01)

(52) U.S. Cl.
USPC ..... Plt./250
CPC ..... *A01H 5/02* (2013.01); *A01H 5/00* (2013.01)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Hydrangea* plant named 'SCHROLL85-09-02', characterized by its compact, upright and mounded plant habit; moderately vigorous growth habit; freely branching habit and strong stems; dark green-colored leaves; large mophead-type inflorescences with red purple-colored sterile flowers; when "blued", that is, treated with aluminum sulfate, sterile flowers are purple in color; long flowering period; and good postproduction quality and longevity.

4 Drawing Sheets

Botanical designation: *Hydrangea macrophylla.*
Cultivar denomination: 'SCHROLL85-09-02'.

BACKGROUND OF THE INVENTION

The present invention relates to a new and distinct cultivar of *Hydrangea* plant, botanically known as *Hydrangea macrophylla* and hereinafter referred to by the name 'SCHROLL85-09-02'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant is a naturally-occurring whole plant mutation of *Hydrangea macrophylla* 'SchrollA03', not patented. The new *Hydrangea* plant was discovered and selected by the Inventor in 2015 as a single flowering plant from within a population of plants of 'SchrollA03' in a controlled greenhouse environment in Aarslev, Denmark.

Asexual reproduction of the new cultivar by softwood cuttings in Aarslev, Denmark since 2015 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL85-09-02'. These characteristics in combination distinguish 'SCHROLL85-09-02' as a new and distinct *Hydrangea* plant:

1. Compact, upright and mounded plant habit.
2. Moderately vigorous growth habit.
3. Freely branching habit and strong stems.
4. Dark green-colored leaves.
5. Large mophead-type inflorescences with red purple-colored sterile flowers; when "blued", that is, treated with aluminum sulfate, sterile flowers are purple in color.
6. Long flowering period.
7. Good postproduction quality and longevity.

Plants of the new *Hydrangea* differ primarily from plants of the mutation parent, 'SchrollA03', in the following characteristics:

1. Plants of the new *Hydrangea* are more freely branching than plants of 'SchrollA03'.
2. Plants of the new *Hydrangea* and 'SchrollA03' differ in sterile flower color as sterile flowers of plants of 'SchrollA03' are dull red in color (not "blued").
3. Plants of the new *Hydrangea* are more tolerant to pathogens and pests than plants of 'SchrollA03'.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the new *Hydrangea* are more compact than and not as vigorous as plants of 'H213901'.
2. Leaves of plants of the new *Hydrangea* are darker green in color than leaves of plants of 'H213901'.

3. Inflorescences of plants of the new *Hydrangea* have more sterile flowers than inflorescences of plants of H213901'.
4. Plants of the new *Hydrangea* and 'H213901' differ in sterile flower color as sterile flowers of plants of 'H213901' are darker red purple in color (not "blued").

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in the following characteristics:

1. Plants of the new *Hydrangea* are less vigorous than plants of 'H213906'.
2. Plants of the new *Hydrangea* are more freely branching than plants of 'H213906'.
3. Plants of the new *Hydrangea* and 'H213906' differ in sterile flower color as sterile flowers of plants of 'H213906' are dark pink in color (not "blued").
4. Plants of the new *Hydrangea* force faster than plants of 'H213906'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SCHROLL85-09-02' grown in a container that has not been "blued".

The photograph at the top of the second sheet is a close-up view of a typical developing inflorescence of 'SCHROLL85-09-02' that has not been "blued".

The photograph at the bottom of the second sheet is a close-up view of a typical developed inflorescence of 'SCHROLL85-09-02' that has not been "blued".

The photograph on the third sheet comprises a side perspective view of a typical flowering plant of 'SCHROLL85-09-02' grown in a container that has been "blued".

The photograph at the top of the fourth sheet is a close-up view of a typical developing inflorescence of 'SCHROLL85-09-02' that has been "blued".

The photograph at the bottom of the fourth sheet is a close-up view of a typical developed inflorescence of 'SCHROLL85-09-02' that has been "blued".

DETAILED BOTANICAL DESCRIPTION

Plants used in the aforementioned photographs and in the following description were grown during the spring in 13-cm containers in a glass-covered greenhouse in Aarslev, Denmark and under cultural practices typical of commercial *Hydrangea* production. Plants of the new *Hydrangea* were pinched one time and were one year old when the photographs and description were taken. During the production of the plants, day temperatures ranged from 15° C. to 25° C., night temperatures ranged from 10° C. to 20° C. and light levels ranged from 40 to 50 klux. In the following description, color references are made to The Royal Horticultural Society Colour Chart, 2007 Edition, except where general terms of ordinary dictionary significance are used.

Botanical description: *Hydrangea macrophylla* 'SCHROLL85-09-02'.

Parentage: Naturally-occurring whole plant mutation of *Hydrangea macrophylla* 'SchrollA03', not patented.

Propagation:

*Type cutting*.—By softwood cuttings.

*Time to initiate roots, summer*.—About twelve days at temperatures about 20° C.

*Time to initiate roots, winter*.—About two weeks at temperatures about 18° C. to 20° C.

*Time to produce a rooted young plant, summer*.—About four weeks at temperatures about 18° C. to 20° C.

*Time to produce a rooted young plant, winter*.—About five weeks at temperatures about 18° C. to 20° C.

*Root description*.—Medium in thickness, fibrous; white, close to N155D, in color.

*Rooting habit*.—Low branching; sparse.

Plant description:

*Plant and growth habit*.—Perennial subshrub; compact, upright and mounded plant habit; broadly inverted triangle; freely branching habit with about five to six lateral branches developing per plant; strong lateral branches; moderately vigorous growth habit.

*Plant height*.—About 25 cm.

*Plant diameter or area of spread*.—About 30 cm to 40 cm.

*Lateral branches*.—Length: About 15 cm to 17 cm. Diameter: About 5 mm to 6 mm. Internode length: About 3 cm to 4 cm. Strength: Strong. Texture: Smooth, glabrous. Color, developing and developed: Close to 144A. Color, lenticels: Close to N199B.

Leaf description:

*Arrangement*.—Opposite, decussate; simple.

*Length*.—About 9 cm to 11 cm.

*Width*.—About 7 cm to 8 cm.

*Shape*.—Ovate to cordate.

*Apex*.—Cuspidate.

*Base*.—Obtuse to rounded.

*Margin*.—Serrate to dentate.

*Texture and luster, upper surface*.—Smooth to rugose, glabrous; semi-glossy.

*Texture and luster, lower surface*.—Rugose, glabrous; prominent venation; matte.

*Venation pattern*.—Pinnate, reticulate.

*Color*.—Developing leaves, upper surface: Close to 137B. Developing leaves, lower surface: Close to 138A. Fully expanded leaves, upper surface: Close to N137A; venation, close to 147C. Fully expanded leaves, lower surface: Close 145A to 145B; venation, close to 145B to 145C.

*Petioles*.—Length: About 1.5 cm to 2 cm. Diameter: About 3 mm. Strength: Strong. Texture, upper and lower surfaces: Smooth, glabrous. Color, upper and lower surfaces: Close to 144C.

Inflorescence & flower description:

*Flower type and habit*.—Showy single sterile and inconspicuous single fertile flowers arranged on terminal mophead-type panicles; panicles hemispherical to flattened globular in overall shape; fertile flowers face upright and sterile flowers face upright to outwardly; early flowering habit, plants begin flowering about ten to twelve weeks after forcing period.

*Natural flowering season*.—Long flowering period, continuous flowering from July throughout the summer until frost in Northern Europe.

*Flower longevity, fertile flowers*.—Flowers last about two to three weeks on the plant; fertile flowers not persistent.

*Flower longevity, sterile flowers*.—Flowers last about four months on the plant; as a cut flower, flowering stems will last about four weeks; sterile flowers persistent.

*Quantity of flowers*.—Freely flowering habit with about 40 to 60 fertile flowers and about 180 to 200 sterile flowers per panicle.

*Fragrance*.—None detected.

*Panicle height*.—About 8 cm.

*Panicle diameter*.—About 15 cm.

*Flower diameter, fertile flowers*.—About 3 mm.

*Flower depth (height), fertile flowers*.—About 2 mm to 3 mm.

*Flower diameter, sterile flowers*.—About 3.5 cm to 4 cm.

*Flower depth (height), sterile flowers*.—About 2 cm.

*Flower shape, fertile flowers*.—Spherical.

*Flower shape, sterile flowers*.—Deltoid.

*Flower buds, fertile flowers*.—Length: About 2 mm to 3 mm. Diameter: About 3 mm. Shape: Spherical. Color: Close to 144C.

*Flower buds, sterile flowers*.—Length: About 3 mm to 4 mm. Diameter: About 2 mm to 3 mm. Shape: Spherical. Color: Close to 144B.

*Petals, fertile flowers*.—Quantity and arrangement: Four to five in a single whorl. Length: About 4 mm. Width: About 2 mm. Shape: Ovate. Apex: Acute. Base: Rounded. Margin: Entire. Texture, upper and lower surfaces: Smooth, glabrous. Color: When opening, upper and lower surfaces: Close to 70C. Fully opened, upper and lower surfaces: Close to 70C.

*Petals, sterile flowers*.—Quantity and arrangement: Four or five in a single whorl. Length: About 3 mm. Width: About 2 mm. Shape: Roughly ovate. Apex: Acute. Base: Truncate, rounded. Margin: Entire. Texture, upper and lower surfaces: Smooth, glabrous. Color: When opening, upper and lower surfaces: Close to 71C; when "blued", close to 95C. Fully opened, upper and lower surfaces: Close to 71C; when "blued", close to 95C; color does not change with development.

*Sepals, fertile flowers*.—Quantity and arrangement: Five in a single whorl; imbricate. Length: About 1 mm to 2 mm. Width: About 1 mm. Shape: Deltoid. Apex: Acute. Base: Truncate. Margin: Entire. Texture, upper surface: Fine pubescence. Texture, lower surface: Smooth, glabrous. Color: When opening and fully opened, upper surface: Close to N144C. When opening and fully opened, lower surface: Close to N144C.

*Sepals, sterile flowers*.—Quantity and arrangement: Three to five in a single whorl; imbricate. Length: About 2 cm to 2.4 cm. Width: About 2 cm to 2.5 cm. Shape: Deltoid. Apex: Acute. Base: Truncated, slightly rounded. Margin: Entire. Texture, upper and lower surfaces: Slightly rippled, glabrous. Color, plants not "blued": When opening, upper surface: Close to 144C to 144D; towards the margins, close to 61B. When opening, lower surface: Close to 144C to 144D; towards the margins, close to N57C to N57D. Fully opened, upper surface: Close to 61B; color does not change with development. Fully opened, lower surface: Close to N57C to N57D; color does not change with development. Color, plants "blued": When opening, upper surface: Close to 144C; towards the margins, close to N79C. When opening, lower surface: Close to 144C; towards the margins, close to N77B. Fully opened, upper surface: Close to N79C; color does not change with development. Fully opened, lower surface: Close to N77B; color does not change with development.

*Pedicels, fertile flowers*.—Length: About 3 mm to 4 mm. Diameter: About 3 mm. Strength: Strong. Aspect: Upright. Texture: Smooth, glabrous. Color: Close to 58C.

*Pedicels, sterile flowers*.—Length: About 2 cm. Diameter: About 2 mm. Strength: Moderately strong. Aspect: Mostly upright. Texture: Pubescent. Color, plants not "blued": Close to 144D tinged with close to 70D. Color, plants "blued": Close to 144D tinged with close to N88D.

*Reproductive organs, fertile flowers*.—Stamens: Quantity per flower: About eight. Filament length: About 1 mm. Filament color: Close to 11D. Anther length: About 1 mm. Anther shape: Reniform. Anther color: Close to 155A. Pollen amount: Abundant. Pollen color: Close to 155A. Pistils: Pistil quantity per flower: About three. Pistil length: About 2 mm. Stigma shape: Oval. Stigma color: Close to 11D. Style length: About 1 mm. Style color: Close to 11D. Ovary color: Close to 11D.

*Reproductive organs, sterile flowers*.—Stamens: Quantity per flower: About eight. Filament length: About 2 mm. Filament color: Close to 164D. Anther length: About 1 mm. Anther shape: Elliptical to reniform, elongated. Anther color: Close to 164D. Pollen amount: Moderate. Pollen color: Close to 18C. Pistils: Pistil quantity per flower: About three. Pistil length: About 2 mm. Stigma shape: Rounded. Stigma color: Close to 164D. Style length: About 1 mm to 2 mm. Style color: Close to 164D. Ovary color: Close to 164D.

*Seeds*.—Quantity: Typically more than 40. Length: About 0.5 mm. Diameter: About 0.2 mm. Color: Close to 164C.

Pathogen & pest resistance: Plants of the new *Hydrangea* have not been observed to be resistant to pathogens and pests common to *Hydrangea* plants to date.

Temperature tolerance: Plants of the new *Hydrangea* have been shown to be tolerant to temperatures ranging from about 4° C. to 35° C.

It is claimed:

1. A new and distinct *Hydrangea* plant named 'SCHROLL85-09-02' as illustrated and described.

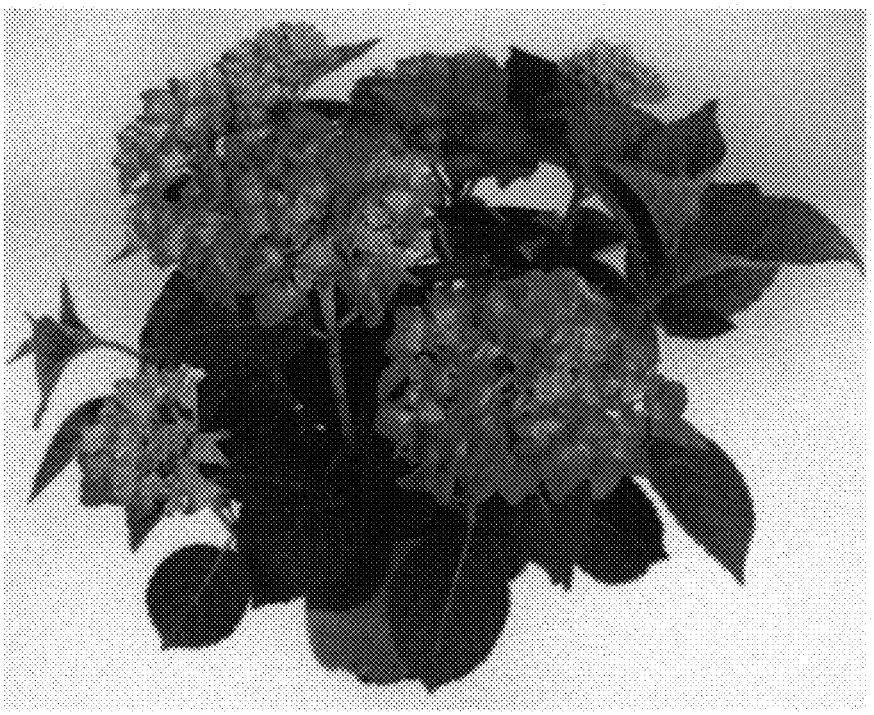

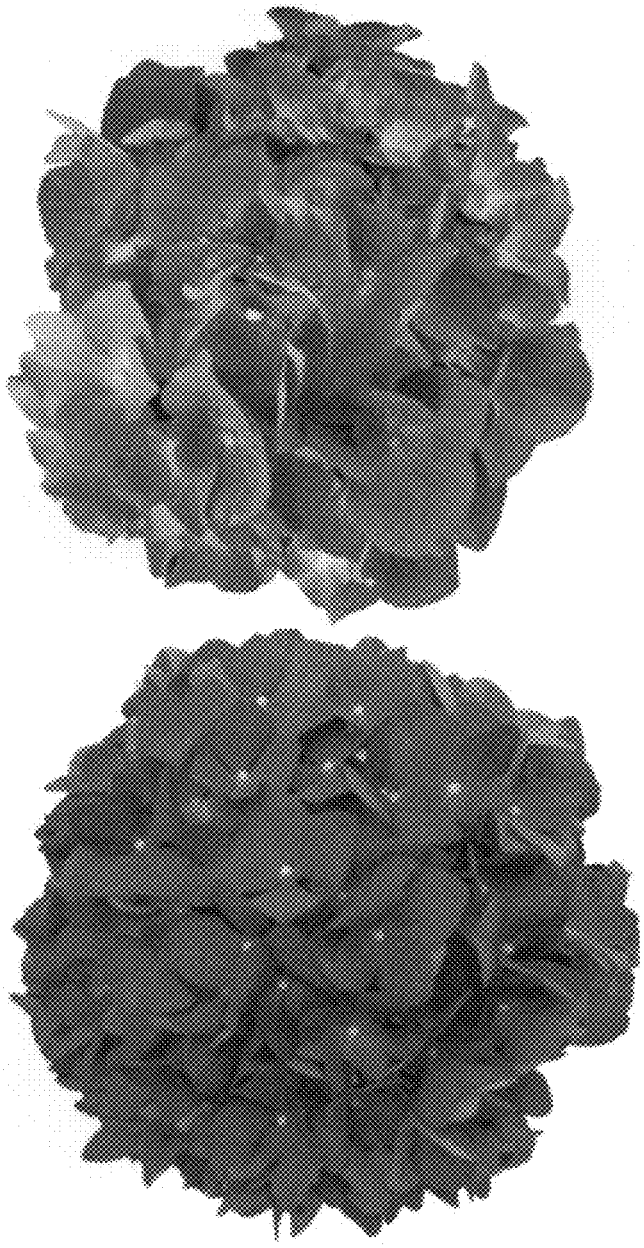

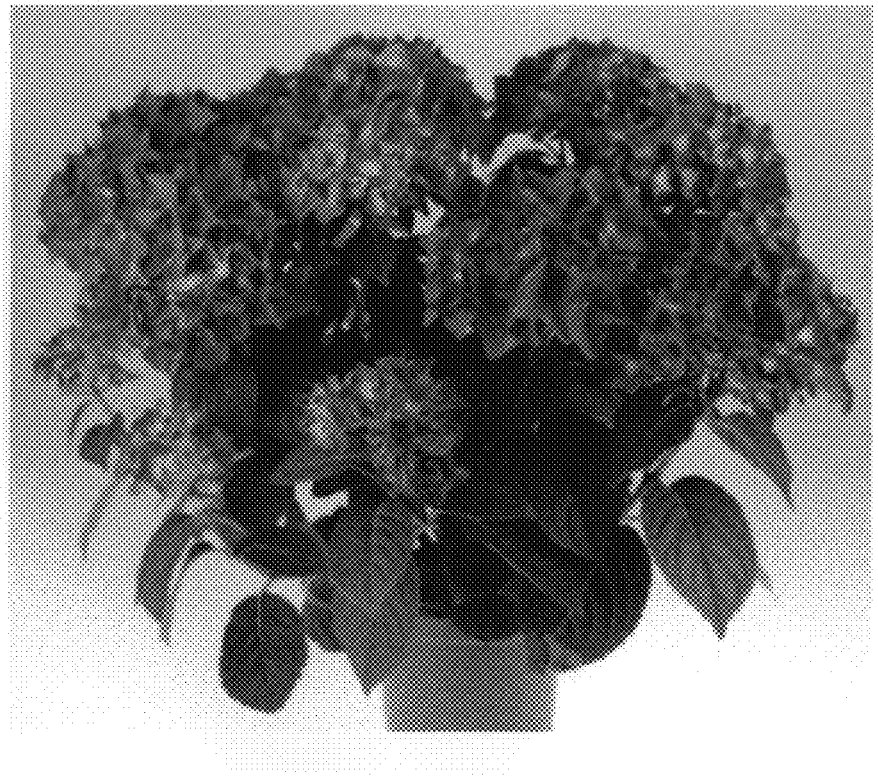

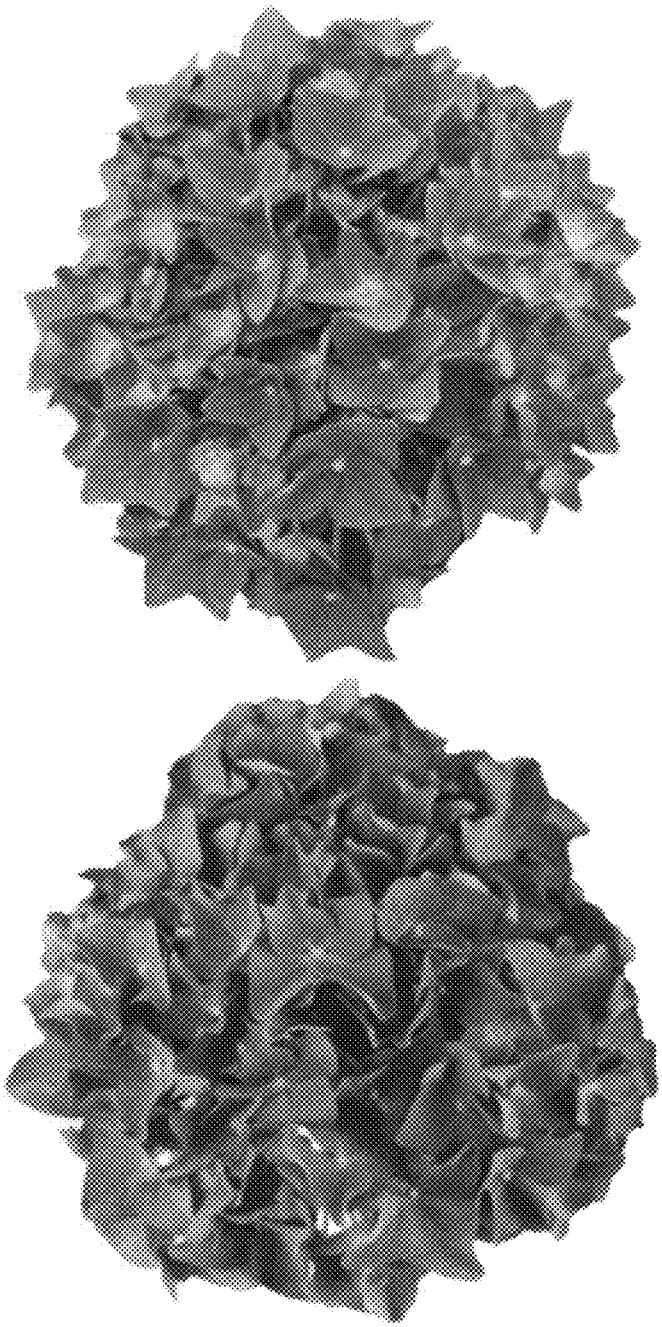

* * * * *